United States Patent
Van Der Kamp et al.

(10) Patent No.: US 9,250,226 B2
(45) Date of Patent: Feb. 2, 2016

(54) METHOD AND DEVICE FOR DETERMINING GREENHOUSE GAS EMISSION FROM A RUMINANT

(71) Applicant: LELY PATENT N.V., Maassluis (NL)

(72) Inventors: Adolf Jan Van Der Kamp, Kampereiland (NL); Leendert Kool, Stolwijk (NL); Patrick Philip Jacob Van Der Tol, Barendrecht (NL)

(73) Assignee: LELY PATENT N.V., Maassluis (NL)

( * ) Notice: Subject to any disclaimer, the term of this patent is extended or adjusted under 35 U.S.C. 154(b) by 0 days.

(21) Appl. No.: 14/259,206

(22) Filed: Apr. 23, 2014

(65) Prior Publication Data

US 2014/0229119 A1    Aug. 14, 2014

Related U.S. Application Data (63) Continuation of application No. PCT/NL2012/050641, filed on Sep. 13, 2012.

(30) Foreign Application Priority Data

Oct. 24, 2011   (NL) ..................................... 2007645

(51) Int. Cl.
  *G07C 11/00* (2006.01)
  *G06F 17/40* (2006.01)
  *G06F 19/00* (2011.01)
  (Continued)

(52) U.S. Cl.
  CPC ............ *G01N 33/497* (2013.01); *A01K 29/005* (2013.01); *G06F 17/40* (2013.01); *G06F 19/00* (2013.01); *G07C 11/00* (2013.01); *Y02W 90/00* (2015.05)

(58) Field of Classification Search
  None
  See application file for complete search history.

(56) References Cited

U.S. PATENT DOCUMENTS

| 5,265,618 A | 11/1993 | Zimmerman |
| 6,868,804 B1 | 3/2005 | Huisma et al. |

(Continued)

FOREIGN PATENT DOCUMENTS

| EP | 1301068 A2 | 4/2003 |
| EP | 2154952 A1 | 2/2010 |

OTHER PUBLICATIONS

Earlier Search Report for NL2007645 issued on Jun. 15, 2012.
(Continued)

*Primary Examiner* — Edward Cosimano
(74) *Attorney, Agent, or Firm* — Oblon, McClelland, Maier & Neustadt, L.L.P.

(57) ABSTRACT

A method for estimating a greenhouse gas emission from a ruminant in a loose housing environment, and in a predetermined time period from T0 to Tdesired, the method including:
  determining a model emission rate function EM(t) for the ruminant
  determining the moments of eating feed by the ruminant, at least during the predetermined time period, as a series of points in time $\{T1, T2, T3, \ldots, Tn\}$
  constructing the estimated real emission rate function ER(t) on the basis of the model emission rate function and the moments of eating feed, and
  integrating ER(t) from T0 to Tdesired.
Also provided is a greenhouse gas emission estimation device, arranged to perform this method. In the device and method, use is made of the insight that knowing the eating moments can fine-tune calculations for establishing greenhouse gas emissions from the animals.

23 Claims, 4 Drawing Sheets

(51) Int. Cl.
*G01N 33/497* (2006.01)
*A01K 29/00* (2006.01)

(56) References Cited

U.S. PATENT DOCUMENTS

| | | | |
|---|---|---|---|
| 7,966,971 B2 * | 6/2011 | Zimmerman | 119/51.02 |
| 8,307,785 B2 * | 11/2012 | Zimmerman et al. | 119/51.02 |
| 2009/0288606 A1 * | 11/2009 | Zimmerman | 119/51.02 |
| 2011/0192213 A1 | 8/2011 | Zimmerman et al. | |

OTHER PUBLICATIONS

International Search Report and Written Opinion for PCT/NL2012/050641 issued on Jan. 14, 2013.
International Preliminary Report on Patentability for PCT/NL2012/050641 issued on Apr. 29, 2014.

* cited by examiner

METHOD AND DEVICE FOR DETERMINING
GREENHOUSE GAS EMISSION FROM A
RUMINANT

CROSS REFERENCE TO RELATED APPLICATIONS

This application is a continuation of PCT application number PCT/NL2012/050641 filed on 13 Sep. 2012, which claims priority from NL application number 2007645 filed on 24 Oct. 2011. Both applications are hereby incorporated by reference in their entireties.

BACKGROUND OF THE INVENTION

1. Field of the Invention

The invention relates to a method for estimating a greenhouse gas emission from a ruminant in a loose housing environment, and in a predetermined time period from T0 to Tdesired, and to a greenhouse gas emission estimation device for estimating a greenhouse gas emission from a ruminant, according to said method.

2. Description of the Related Art

Enhanced greenhouse gas (GHG) emissions are deemed to be a cause of an enhanced greenhouse effect. Emissions by dairy animals are believed to contribute a large part of the enhanced greenhouse gas emissions, not only via manure but also, and believed mainly, via eructation of methane. Therefore, it is important to know the emission of such greenhouse gases in dairy animals, for knowing the emissions is a necessary first step of controlling and reducing such emissions.

In the art, significant research has been conducted to try and determine the GHG emission of individual dairy animals in a controlled environment, such as completely sealed cabins, in which the complete emission of the animal could be measured and analyzed. However, in a normal dairy environment, useful models are scarce and mainly indirect such as through fatty acid profiles from milk.

BRIEF SUMMARY OF THE INVENTION

It is an object of the invention to provide a useful model for the determination of greenhouse gas emissions of dairy animals in their normal environment, in particular in a loose housing environment.

The invention, in an embodiment, provides a solution for this object in a method comprising: determining a model emission rate function EM(t) for the ruminant, determining the moments of eating feed by the ruminant, at least during the predetermined time period, as a series of points in time $\{T1, T2, T3, \ldots, Tn\}$, constructing the estimated real emission rate function ER(t) on the basis of the model emission rate function and the moments of eating feed, and integrating ER(t) from T0 to Tdesired. In this way, the various eating moments are taken into account as regards their effect on the emission. The invention's insight is to apply a fresh "start", each time that the animal eats, and to determine the total as the sum over a consecutive series of such fresh starts. The inventors' work indicates that a useful approximation of total emission can be obtained with such a model. The inventors have found that each moment of eating starts a new "cycle" of GHG emissions, which has an effect on total emissions in a certain time period. For example, in case there are more eating moments in that time period, there is very likely also an increased output of GHG, and vice versa.

It is noted, that the model emission rate function should be taken to have a peak value some time after the eating moment. This reflects the fact that, when new feed is eaten, the digestion that is to produce GHG will need some time to do so. This will work to a peak, after which the gradually decreasing amount of feed still to be digested will cause a decrease of the emitted GHG.

In an embodiment, a method for estimating a greenhouse gas emission from a ruminant in a loose housing environment, and in a predetermined time period from T0 to Tdesired, is provided, wherein the method comprises:

determining a model emission rate function EM(t) for the ruminant determining the moments of eating feed by the ruminant, at least during the predetermined time period, as a series of points in time $\{T1, T2, T3, \ldots, Tn\}$ constructing the estimated real emission rate function ER(t) on the basis of the model emission rate function and the moments of eating feed, and integrating ER(t) from T0 to Tdesired.

In an embodiment, the function ER(t) is constructed as $ER(t)=EM(t-T1-C1)$ for $T1 \leq t < T2$, $EM(t-T2-C2)$ for $T2 \leq t < T3$, $\ldots$, $EM(t-Tn-1-Cn-1)$ for $Tn-1 \leq t < Tn$, and $EM(t-Tn-Cn)$ for $Tn \leq t$, wherein $C1, C2, \ldots, Cn$ are constants.

In an embodiment, all constants are zero.

In a further embodiment, all constants $C1 \ldots Cn$ are determined such that the function ER(t) is a continuous function.

In an embodiment, the function ER(t) is constructed as $$ER(t) = \sum_{i=1}^{n} EM(t - Ti)$$

for all eating moments $T1, \ldots, Tn$ relevant for the desired period of time T0–Tdesired.

In a further embodiment, the feed is ration containing roughage.

In another embodiment, the feed further contains concentrates.

In an embodiment, determining the model emission rate function comprises:

measuring a greenhouse gas emission rate at a plurality of measurement points in time $TM0, \ldots, TMn$, providing respective values $EM0, \ldots, EMn$ establishing for each of said measurement points in time $TM0, \ldots, TMn$ the most recent feeding moment $TF0, \ldots, TFn$ before the respective measurement point in time, and determining the function ER(t) by fitting a mathematical curve that fits through the sets of values $((TM0-TF0), EM0), \ldots, ((TMn-TFn), EMn)$.

In an embodiment, the method further comprises repeating the steps of measuring at an additional point in time Tadd said greenhouse gas emission rate EMadd, and redetermine the function by adapting and refitting the mathematical curve through one of the last X sets of values of TM and EM, wherein X is a predetermined number, and all sets of values of TM and EM.

In an embodiment, in the step of redetermining the function, one or more predetermined constraints are applied, comprising predetermined rules with respect to the relative or absolute change of one or more coefficients used in the function.

In an embodiment, the mathematical curve is selected from a set of standard curves depending on the type or race of animal, and wherein the fitting comprises multiplying the curve by a constant (F).

In a further embodiment, determining the moments of eating feed comprises determining the moments when at least one of the following conditions is met:
new ration is provided to the ruminant
feed is displaced towards a feed fence at which the ruminant is allowed to feed
the ruminant is provided access to a pasture.

In an embodiment, determining the moments of eating comprises identifying the ruminant at a feeding place and determining that said ruminant is eating, by means of a eating sensor.

In a further embodiment, the eating sensor comprises a camera with image processing software for recognizing eating behaviour, a feed weight sensor arranged to determine a weight change in a feeding device, or a microphone with sound processing software for recognizing eating behaviour.

In another embodiment, determining the moments of eating comprises determining when the ruminant produces eating sounds by means of a sound sensor, that is designed to detect sounds produced by the ruminant when moving its mouth in particular for chewing.

In an embodiment, when determining the moments of eating, rumination sounds are excluded.

In an embodiment, when determining the moments of eating, only rumination sounds are detected, and the moments of eating are determined to be the moments of a local minimum in rumination sounds.

In an embodiment, the method further comprises:
providing a herd having a plurality of ruminants
providing one or more ruminant ID devices, at least at one or more positions for feeding the ruminants and at one or more positions for measuring a greenhouse gas emission rate and arranged to identify the ruminant and provide an ID signal
performing the method for each of the ruminants in the herd, and
providing a total greenhouse gas emission in the predetermined time period as the sum of the greenhouse gas emissions from each of the ruminants.

In an embodiment, a greenhouse gas emission estimation device for estimating a greenhouse gas emission from a ruminant is provided, the device comprising:
at least one greenhouse gas emission rate sensor, arranged to provide a greenhouse gas emission rate signal
a clock device arranged to provide a time signal each time when said ruminant eats and each time when the at least one greenhouse gas emission rate sensor measures a greenhouse gas emission rate signal
a control unit, configure to
determine a model emission rate function $EM(t)$ for the ruminant
determine the moments of eating feed by the ruminant, at least during a predetermined time period, as a series of points in time $\{T1, T2, T3, \ldots, Tn\}$
constructing an estimated real emission rate function $ER(t)$ on the basis of the model emission rate function for the ruminant and the moments of eating feed by the ruminant, and
integrating $ER(t)$ from $T0$ to $Tdesired$.

In an embodiment, each greenhouse gas emission rate sensor comprises or is provided together with a ruminant ID device arranged to establish the ID of a ruminant upon visiting the sensor.

In an embodiment, a feeding unit with an animal ID station arranged to identify the ruminant upon feeding is provided, the control unit arranged to process the corresponding time signal together with the animal ID.

In a further embodiment, there is provided a greenhouse gas emission sensor with an animal ID station at one or more of a milking place, at a feeding place or at a resting place.

Advantageous or otherwise special embodiments are mentioned in the dependent claims.

In embodiments, the function $ER(t)$ is constructed as $ER(t)=EM(t-T1-C1)$ for $T1 \leq t < T2$, $EM(t-T2-C2)$ for $T2 \leq t < T3, \ldots, EM(t-Tn-1)$ for $Tn-1 \leq t < Tn$, and $EM(t-Tn-Cn)$ for $Tn \leq t$, wherein $C1, C2, \ldots, Cn$ are constants. In this way, after each eating moment, a similar shape of the emission curve is constructed, as the emission mechanism, stemming from the particular animal, does not change itself. One could also say that between each set of subsequent eating moments, a new emission curve is set up, but in each case based on the same basic curve shape. The constants serve to adapt the curve parts to specific circumstances or approximations, as will be explained further below.

In a particular embodiment, all constants are zero. In this approximation, each previous curve is simply cut off at a new eating moment, and the curve starts anew from zero emission at that new eating moment. This is a very simple approximation, and easily implemented mathematically. Still, however, especially since in practice most curves will show a peak emission very shortly after the eating moment, this is already a useful approximation.

In other embodiments, all constants $C1 \ldots Cn$ are determined such that the function $ER(t)$ is a continuous function. This holds in particular for the eating moments, i.e. the transition points. In practice, the emission function will be a continuous function, just like any other physical quantity. Therefore, an approximation that will take this into account can be a better approximation. In this embodiment, a previous curve part will have a certain value at a certain time after its corresponding starting eating moment. In this embodiment, it is assumed that the curve part for the subsequent interval, i.e. after the following eating moment, will start at that same value. Note that this still leaves two possibilities, one before the peak value, and one after the peak value. It is assumed that the value before the peak is taken, leading to a corresponding value for the corresponding constants $C1, C2, \ldots$ The above shows just a number of possible embodiments of the general idea of the invention. Others could be to simply add a new curve to the existing one. In other words, all emission curves started before a new eating moment are allowed to go on indefinitely, while the value for a new curve, starting at the new eating moment, is added for each time after that new eating moment. Therefore, in an additional embodiment, the function $ER(t)$ is constructed as $$ER(t) = \sum_{i=1}^{n} EM(t - Ti)$$

for all eating moments $T1, \ldots, Tn$ relevant for the desired period of time $T0-Tdesired$. Note that this encompasses the case that even $T1$ is after $T0$, leaving the first time part from $T0$ to $T1$ open to some uncertainty. It also encompasses the case of one or more eating moments $T1, T2, \ldots$ before $T0$. The relevant time frame to be taken into account before $T0$ depends on how quickly the function $EM(t)$ falls to zero. If that is a period $Tfall$, then preferably all eating moments up to $Tfall$ before $T0$ should also be taken into account, as the first eating moments $T1, T2, \ldots$. However, if that time is only a small part of the total period of time $T0-Tdesired$, it may safely be ignored.

Note that the step of integrating is deemed to encompass all mathematical equivalents thereof, among others the approximation of summing a number of points times the width of the relevant intervals et cetera. Also note that it is necessary for the most precise estimation, to determine all moments of eating. However, it is possible to miss one or more moments, allowing for a less precise approximation. Also, an estimate between T0 and T1 for T0<T1 is not possible, and is left out. In such a case, some (more general) approximation for the first interval should be made, or the time and eating moments should be selected such that this situation does not occur. Note that it is also possible in the present model to have more than one measurement of GHG emissions between two eating moments. Such apparently additional measurements then serve to make the model more precise.

In particular embodiments, the feed is ration, containing roughage such as grass, hay, silage, maize, and optionally containing concentrates. Herein, the concept of "ration" is deemed to comprise the so-called TMR, or total mixed ration, as well as PMR, or partial mixed ration. All these rations comprise roughage, while some also comprise concentrates. It is believed by the inventors that these non-"concentrates only" feeds provide the main GHG emissions. Concentrates only feeds, such as given in for example milking parlours or dedicated concentrate feeding parlours, are to be excluded. It is believed that "concentrates only" feeds will have an effect on the total GHG emissions, but what that effect is, is not yet known.

In explaining the invention above, a part comprises determining a model emission rate function for the animal. In embodiments, determining the model emission rate function comprises measuring a greenhouse gas emission rate at a plurality of measurement points in time $TM0, \ldots, TMn$, providing respective values $EM0, \ldots, EMn$, establishing for each of said measurement points in time $TM0, \ldots, TMn$ the most recent feeding moment $TF0, \ldots, TFn$ before the respective measurement point in time, and determining the function $ER(t)$ by fitting a mathematical curve that fits through the sets of values $((TM0-TF0), EM0), \ldots, ((TMn-TFn), EMn)$. In itself, the mathematical technique of fitting a curve to various points is well-known. However, according to the present invention, it is understood that all measured points can be related to a single curve, the (model) emission rate function. As said above, this is based on the insight that, at least on average, the GHG mission for a dairy animal will always show the same behaviour after eating. Therefore, it does not matter when the GHG emission (rate) is measured, as long as it is measured. As a remark to be made here, the inventors believe that the actual amount of feed consumed may have an influence on the production of GHG. However, to the inventors' knowledge, there is not known a clear description of any mathematical connection between amount of feed and GHG emissions.

In an important further development of the invention, the method further comprises repeating the steps of—measuring at an additional point in time Tadd said greenhouse gas emission rate EMadd, and—redetermine the function by adapting and refitting the mathematical curve through one of the last X sets of values of TM and EM, wherein X is a predetermined number, and all sets of values of TM and EM. The former case represents something of a rolling average emission rate function, while the latter represents a more general average function. With this embodiment, it is possible to update the emission rate function to new values. This not only allows an improved accuracy, but also allows dynamic adaptation of the function/the curve to changes in the animal, such as might follow from development of the body of the animal, e.g. maturing or its lactation cycle, or a change in diet, seasonal changes and so on.

In a particular embodiment, in the step of redetermining the function, one or more predetermined constraints are applied, comprising predetermined rules with respect to the relative and/or absolute change of one or more coefficients used in the function. In this embodiment, care is taken that the function, i.e. the model emission rate function $EM(t)$, does not change too wildly. A particular approach to applying such constraints is the so-called DLM method, or dynamic linear modeling. For an example, reference is made to EP2154952, relating to a DLM model for feeding dairy animals. More in particular, this example is based on Bayesian rules for adapting the model. Such Bayesian rules may also advantageously be applied as the constraints to be applied in the model of the present invention.

In the present invention, use is made of a standard curve for emission $EM(t)$ for each animal. This is a first approximation. In a particular further development, the method is refined in that the mathematical curve is selected from a set of standard curves depending on the type or race of animal, and wherein the fitting comprises multiplying the curve by a constant. This allows the following advantage. Although it is assumed that the basic shape of the emission function $EM(t)$ is basically the same for all animals at least of a certain type or race, there may be variations within such a type or race of animals. For example within the race Holstein-Friesian, there may be a small or extra large animal. This might simply be the result of age, or of genetic variation in the final dimensions. Nevertheless, this embodiment assumes that the basic curve may then be scaled up or down by a constant. This constant is to be determined from a number of measurements. For example, the first 3-10 measurements are used to determine the constant (factor) for scaling the standard curve for Holstein-Friesian cows, selected from the set of standard curves. This can be done by fitting those measurements to the standard curve, with the scaling factor is the variable for fitting. The resulting fitting factor, applied to the standard curve, then gives the "adapted standard curve" for that specific animal, which will lead to more accuracy. Of course, other ways of fitting to the standard curve are not excluded, such as a shorter or longer time delay between eating moment and peak of the emission curve.

One of the steps in the method is determining the moments of eating of the feed. In embodiments, determining the moments of eating feed comprises determining the moments when at least one of the following conditions is met: new ration, excluding concentrates only feed, is provided to the ruminant; feed is displaced towards a feed fence at which the ruminant is allowed to feed; the ruminant is provided access to a pasture. Herein, the choice is made that the eating moments are the starting moments. It may also be argued that the moments of eating should be the average of the period of time during which the condition is met, or a predetermined time after the first moment the condition is met. Although the inventors made a choice for the first moment, this is done more out of practicality than for other specific reasons. For GHG emissions do not start to increase at the very moment of the starting to eat, as they at least require digestion down the digestive tract. It should be noted, therefore, that the above-mentioned alternative moments are also deemed to be within the scope of the present invention.

In particular embodiments, determining the moments of eating comprises identifying the ruminant at a feeding place and determining that said ruminant is eating, by means of a eating sensor. In some barn layouts, there are specific individual feeding stations for feeding ration. As these provide individually adapted rations to the animals, they are ideally suited to provide specific information on eating moments. By the way, such individual feeding stations are also ideal to determine GHG emission, since there is no interference from other animals. Note that the emission is deemed to be caused by previous eating. All this will be explained further below.

In some embodiments, the eating sensor comprises a camera with image processing software for recognizing eating behaviour, a feed weight sensor arranged to determine a weight change in a feeding device, and/or a microphone with sound processing software for recognizing eating behaviour. These have proved useful ways of determining when an animal eats. For example, if the image processing software establishes that the animal repeatedly puts its mouth where the feed is, it is safe to assume that it is eating. If the, commonly known, feed weight sensor establishes a change in the feed weight, the animal must have eaten. As to the microphone with sound processing software, reference is made to EP1301068, which discloses a sensor able to distinguish between ruminating and eating. Thereby, eating actions may be established.

In embodiments, determining the moments of eating comprises determining when the ruminant produces eating sounds by means of a sound sensor, in particular provided on or near the neck and/or mouth, that is designed to detect sounds produced by the ruminant when moving its mouth in particular for chewing. This is a somewhat more particular embodiment as mentioned before. Again, reference is made to EP1301068 for more particulars. Also, as already mentioned above, when determining the moments of eating, rumination sounds are to be excluded, as these are not believed to have a major influence on GHG emissions.

In particular, it is possible to include detecting whether the ruminant is standing up or lying down, and neglecting moments/periods with sounds produced when lying down, more in particular detecting whether the head of the ruminant is lowered to the ground, and neglecting moments/periods with sounds produced while the head is not lowered during at least a predetermined time. All this serves to select the moments of actual eating, and leaving out other activities. Herein, it is assumed that it is relatively rare that the animal ruminates while standing up, and to further exclude this situation, which is not impossible, it is assumed that the combination of standing up, ruminating and the head towards the ground is really to be neglected. In other words, if the animal produces eating sounds while standing up and the head is down, this is deemed definitely eating.

In other embodiments, the method comprises that, when determining the moments of eating, only rumination sounds are detected, and the moments of eating are determined to be the moments of a local minimum in rumination sounds. Again, the rumination sensor as disclosed in e.g. EP1301068 may be used to determine periods when the animal ruminates. It was found a good approximation of the eating moments to take the time of minimum rumination activity, inbetween periods of rumination. This embodiment is not applicable in loose housing systems, but in particular also in systems where, at least during part of the day, but also during longer periods before returning to the housing, the cows graze on pastures. On pastures, it is more difficult to determine exact eating moments. However, by using a rumination sensor, it is still possible to determine the moments by the method just described. Note that such rumination data may be sent to a central computer, by Bluetooth™ or other transmitting devices.

In advantageous embodiments, the method comprises:
providing a herd having a plurality of ruminants
providing one or more ruminant ID devices, at least at one or more positions for feeding the ruminants and at one or more positions for measuring a greenhouse gas emission rate and arranged to identify the ruminant and provide an ID signal
performing the method for each of the ruminants in the herd, and
providing a total greenhouse gas emission in the predetermined time period as the sum of the greenhouse gas emissions from each of the ruminants.

With this embodiment, the GHG emissions may be determined for a whole herd, instead of just one animal. It is understood that for each animal it is possible to take the same standard curve EM(t) for constructing the individual curve ER(t), but it is of course also possible, and more accurate, to use individualized curves as described further above. By thus knowing the total GHG emissions of the herd, possible effects of diet or otherwise may be studied. This knowledge may be used to see if it is possible to reduce the total GHG emissions.

In the present method, the animal can be any ruminant animal, such as buffaloes, goats, and so on. In particular however, the ruminant is a cow. Furthermore, the greenhouse gas may be any gas that is emitted by the animal that has an effect on the enhanced greenhouse effect, such as carbon dioxide and methane. In particular, however, the GHG in the present method is methane, as this is not only a gas with a much bigger relative effect on the enhanced greenhouse effect, with a global warming potential of 25 times that of carbon dioxide, over a period of 100 years, but it is furthermore more strictly related to digestion, thereby providing more direct information thereabout. Contrarily, carbon dioxide is also, and maybe predominantly, related to burning bodily fuel. Thus any information from carbon dioxide relating to digestion should be filtered out, which is not an easy step.

The invention also relates to a greenhouse gas emission estimation device for estimating a greenhouse gas emission from a ruminant, according to a method of any of the preceding claims, the device comprising:
at least one greenhouse gas emission rate sensor, arranged to provide a greenhouse gas emission rate signal
a clock device arranged to provide a time signal each time when said ruminant eats and each time when the at least one greenhouse gas emission rate sensor measures a greenhouse gas emission rate signal
a control unit arranged to apply the method of any preceding claim, and on the basis of the measured time signals and greenhouse gas emission rate signals.

This device applies the method of the present invention, with a principal advantage of supplying useful information on (total) emission of GHG in a simple way.

In embodiments, each greenhouse gas emission rate sensor comprises or is provided together with a ruminant ID device arranged to establish the ID of a ruminant upon visiting the sensor. This is useful for coupling the measured emission to a particular animal, especially in an environment where there are more animals.

Advantageously, the device comprises a feeding unit with an animal ID station arranged to identify the ruminant upon feeding, the control unit being arranged to process the corresponding time signal together with the animal ID. Herein, the ID station identifies the animal and couples a clock signal, i.e. eating moment signal, to the ID. Note that a similar signal may be obtained otherwise, such as with a feed fence with an ID station, or a feed fence with a feed pusher having a control with a clock. Herein, when the feed pusher pushes feed towards the feed fence, according to e.g. a programmed route, it appears that the animals start eating anew. Thus, an eating moment is deemed present upon the feed pusher pushing feed.

In embodiments, there is provided a greenhouse gas emission sensor with an animal ID station at one or more of a milking place, at a feeding place, such as a feeding box or feeding fence, and/or at a resting place. For the present invention, there needs to be at least one GHG sensor. Preferably, such sensor is positioned in a way in which an animal is more or less separated from the others. In this way, emissions from other animals will not, or to an acceptable extent, interfere with the emission to be measured. Advantageously, a milking box and/or feeding box comprise such a GHG emission sensor. Having multiple sensors spread throughout the housing may be advantageous, as this may provide a larger set of measurements during the relevant time period.

BRIEF DESCRIPTION OF THE DRAWINGS

The features and advantages of the invention will be appreciated upon reference to the following drawings, in which.

DESCRIPTION OF ILLUSTRATIVE EMBODIMENTS

Figure 1:
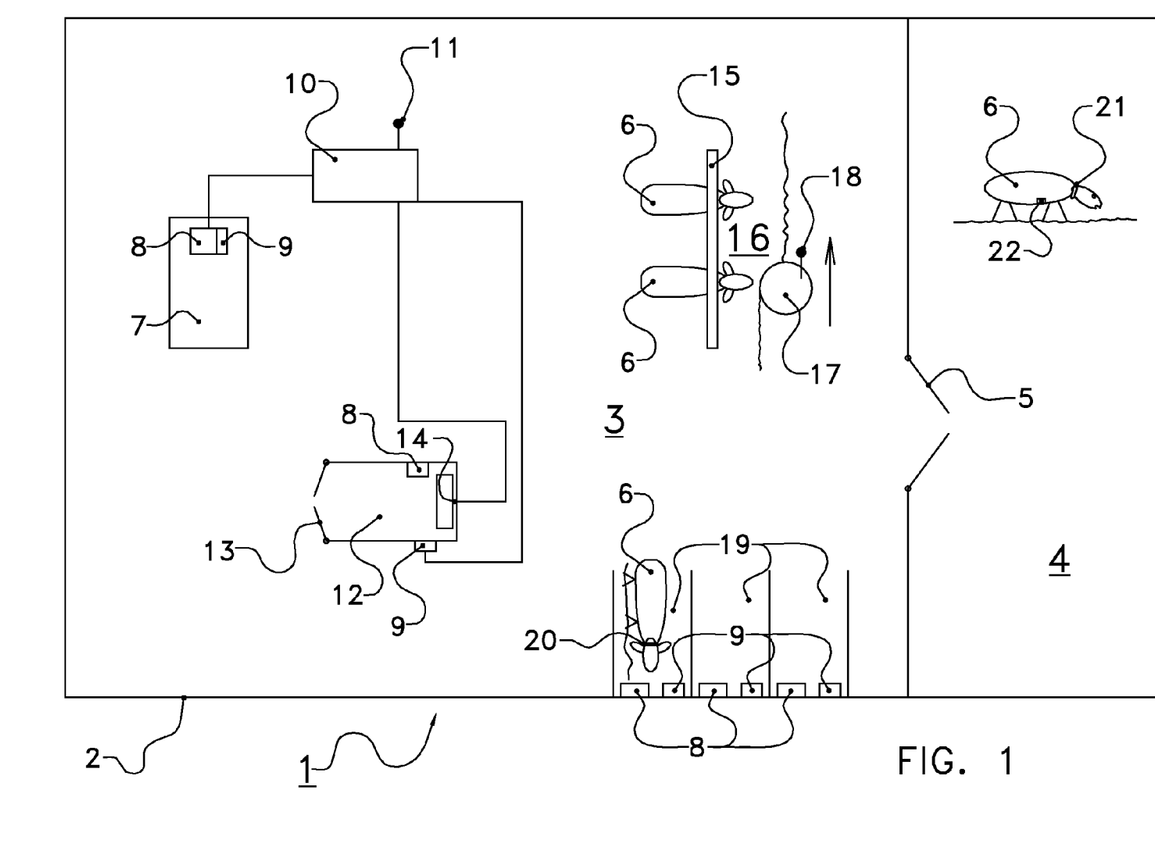
FIG. 1 is a diagrammatic drawing of a loose-housing system according to the invention.

The following is a description of certain embodiments of the invention, given by way of example only and with reference to the drawings. FIG. 1 is a very diagrammatic drawing of a system 1 with a housing 2 with a stable 3 and optional pasture 4 with gates 5 there between. Cows are denoted by 6.

Reference numeral 7 indicates a milking robot with a gas sensor 8 and an ID device 9, all connected to a computer 10, here shown to comprise a transceiver 11. A feeding box 12 is shown, with gates 13, a feed trough 14, as well as a gas sensor 8 and ID device 9.

A feed fence is indicated at 15, with feed 16 being pushed by a feed pusher 17, also having a transceiver 18. Cubicles are indicated by 19, in one of them a cow with an ID tag 20.

At the pasture, a cow is grazing, wearing a rumination sensor 21 and a height sensor 22.

In the housing, an important part is the milking robot 7. Here, the animals are milked and optionally fed concentrates. When visiting the milking robot, the animals are identified with the ID device 9. Additionally, the milking robot comprises a GHG sensor 8, in particular a methane sensor, arranged to measure (greenhouse) gas emission from an animal in the milking robot 7. For examples of such gas sensors, which are known per se, reference is made to document US2011/0192213, in particular e.g. paragraph 0018. Also, as is described in this document, it is possible to monitor the ratio of carbon dioxide and methane in order to obtain an indication for the absolute emission of methane. Note that it is seen as an advantage when no bolus is used to determine GHG emission, such as those using slow release of SF6 as a tracer gas. No bolus means a more natural behavior.

A similarly important part may be played by the feeding box 12. This may similarly comprise an animal ID system, as well as a gas sensor 8 as described above. In the feeding box 12, roughage may be provided to an animal when visiting and identified by the ID device 9. Not only does this serve to offer the best ration available for the animal, but it also ensures that the eating moment is recorded with high accuracy. This may be achieved through e.g. a weight sensor for the trough, that registers eating moments when the feed weight diminishes. Simultaneously, GHG emissions are measured by the sensor 8, and combined with a timing signal.

It is noted that the computer 10, as well as each ID device 9, will have a clock device for recording moments in time.

The information from both the milking robot 7 and the feeding box 12 are sent to a central computer 10, where it is processed according to the invention, to be explained in connection with FIGS. 2-4.

In addition, there are provided cubicles 19 for cows 6 to lie down and ruminate. Shown here is only one cow 6 in a cubicle 19. The cow carries an ID tag 20, with which she is identified by the ID device 9. A local gas sensor 8 again serves to determine a GHG emission from that cow. It is remarked here that it is only optional to provide so many gas sensors 8, as in principle one would do.

The feed fence 15 shown in the FIG. 1 serves for the cows 6 to get feed 16, in particular ration, such as hay or the like. There may be added some concentrates. Also shown is a feed pusher 17, such as the Lely Juno™ (Lely Patent N.V., Maassluis, The Netherlands), that is arranged to push the feed 16 towards the feed fence 15, i.e. towards the cows 6. It is remarked in practice that the pushing of the feed 16 is a trigger for the cows to come to the fence 15 and eat. Therefore, if the fee pusher 17 pushes, this is considered an eating moment, for all practical purposes. The feed pusher, programmed to follow certain routes and during certain times of day, will send a clock or timing signal to the central computer 10 via their respective transceivers 18 and 11, such as a Bluetooth™ connection or the like. The central computer will handle that signal from the feed pusher as an eating moment.

There is also shown a pasture 4, with gates 5. If these gates are automatic, their opening, combined with a time signal, may be considered an eating moment, as the cows being presented with fresh grass may for all practical purposes be considered the start of eating said grass. Alternatively or additionally, the cows 6 may be provided with a rumination sensor 21. If this sensor 21 is arranged to discern eating sounds and rumination sounds, as disclosed in EP1301068, then sending a signal whenever there is an eating moment suffices. However, even in cases when only rumination sounds are detected, an eating moment may be inferred, in particular by the central computer to which the signals may be sent, e.g. by Bluetooth™. For the computer may infer the periods of time when there is minimal rumination activity, in between periods with high rumination activity. In practice, the moments of minimal rumination activity can be taken to be the eating moments. These are also stored by the computer 10. Moreover, also shown is a height sensor 22, arranged to determine whether the cow 6 is standing. In combination with the rumination sensor 21, this may well distinguish between eating and ruminating, as a cow will hardly ruminate when standing up, in particular if the height sensor 22 and/or the rumination sensor 21 is additionally able to tell whether the cow has her head towards the ground.

Thereby, the total system 1 can determine the moments when an animal eats, either at the roughage trough 14 or at the feed fence 15, and even in the pasture 4. It furthermore establishes the GHG emissions of an animal (ID controlled) at various moments in the milking robot 7, and/or the feeding box 12 and/or in the cubicles 19.

Figure 2:
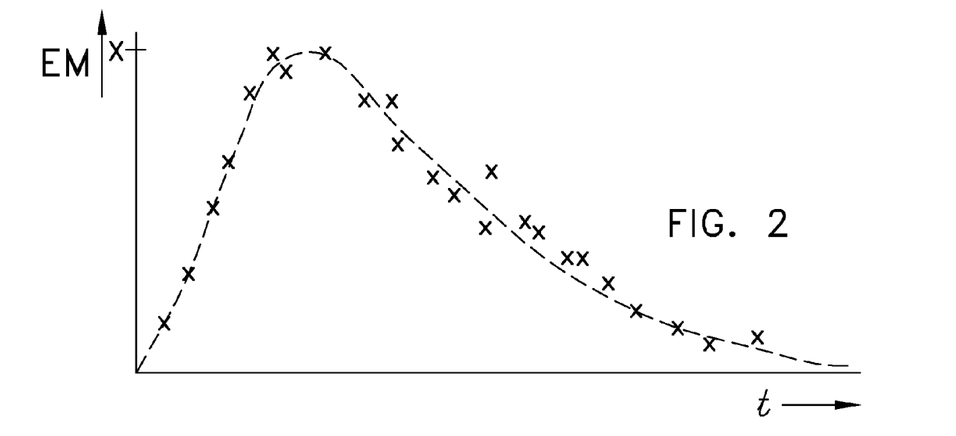
FIG. 2 is graph for determining the basic function EM(t) based on measurements.

With the help of the above data, the system determines a scatter plot of GHG emissions versus time after an eating moment, in FIG. 2. Note that this figure relates either to the data for one animal, or (less preferably) for one type of animal. Next, on the basis of a selected basic model function, a mathematical curve is fitted through the data (the dashed line). As a basic model function, one could take e.g. EM(t)=P(t)·exp(−t) wherein P(t) is a polynomic function of a desired order, such as a first or second order. A concrete example would thus be EM(t)=4·t^2·exp(−t). In any case, it should be a function beginning at zero, having a maximum, and then slowly falling off to zero again, to reflect the natural course of normal GHG emissions.

Figure 3:
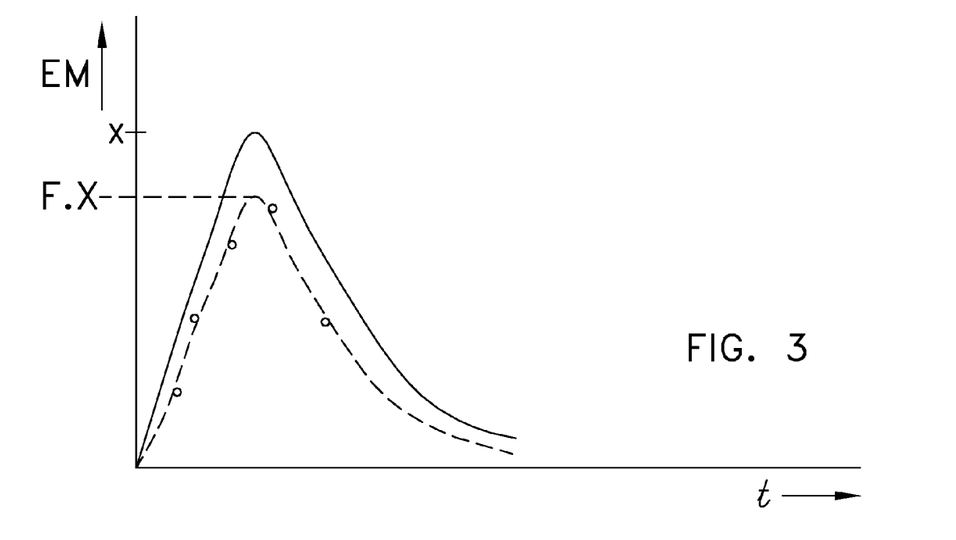
FIG. 3 is a graph for determining an individual function EM(t) for a specific animal, again based on measurements.

In an optional step, relating to FIG. 3, this basic function EM(t), which holds for example for a certain race of cows, such as Jersey or Holstein, may be optimized for an individual animal. Suppose that the general function EM(t) has been established for an average animal of that type. This is shown in the FIG. 3 as the solid line, peaking at a value X (relative units). Now, for a particular animal, a number of emission values have been established, shown as the five circles. Then, a curve is fitted, that has the same shape, but is multiplied by a fixed constant F. This individualized curve is shown as the dashed line, which thus peaks at a value F·X. It is of course possible to use different fitting techniques to establish the individual curve, but this suits fine. Note that F is shown to have a value smaller than 1. It may of course also be larger than 1 for other animals.

Figure 4:
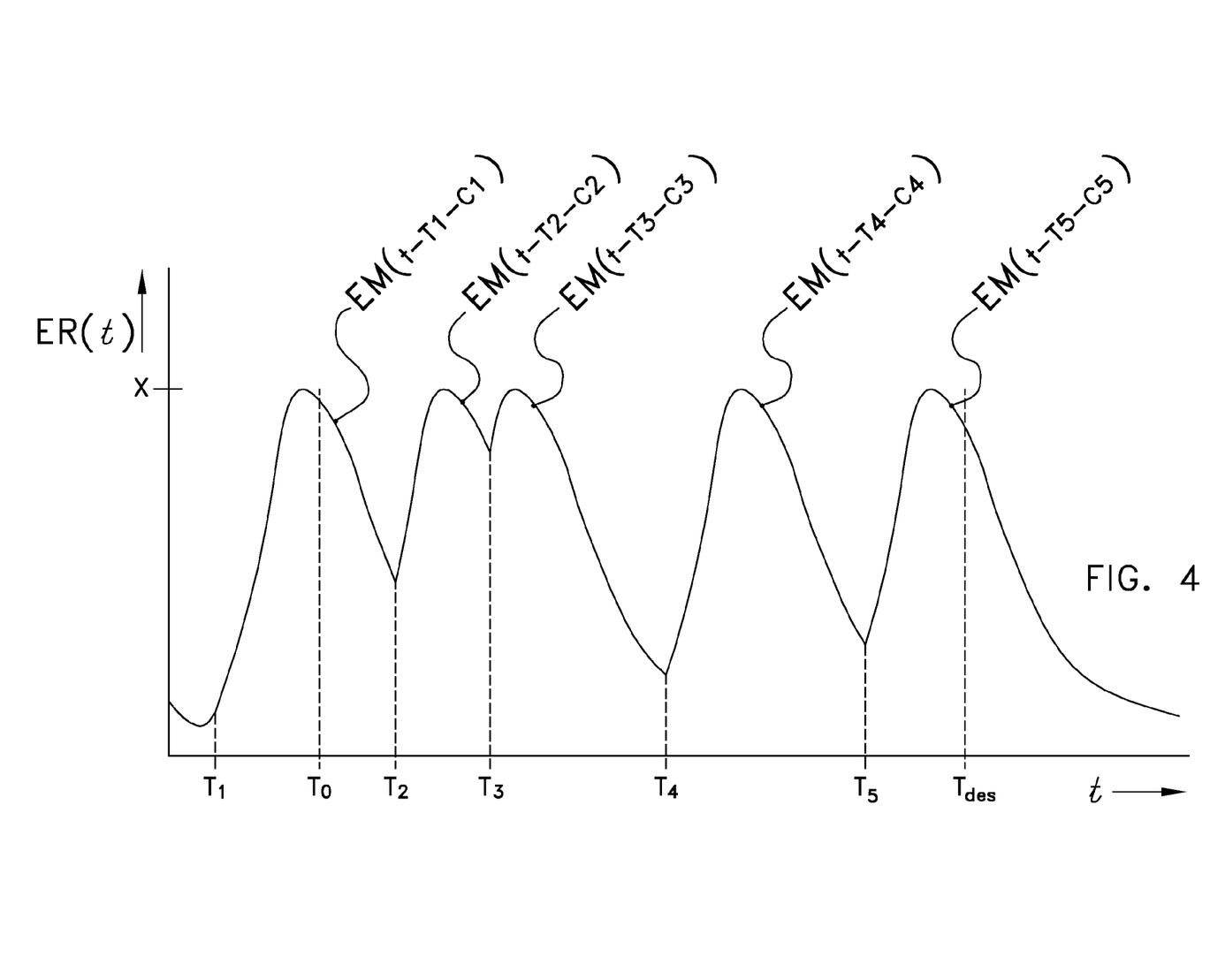
FIG. 4 is a graph showing a constructed function ER(t), according to the invention.

Then, in FIG. 4, this function EM(t), optionally individualized, is plotted for various time intervals, each starting and ending with subsequent eating moments, such that a continuous mathematical function ER(t) is obtained. Thereto, from a first eating moment T1, one arbitrarily starts from zero or a zero measurement, and the function EM(t) is plotted from t=T1. This is cut off at t=T2. At such time T2, the function for the first interval will have a certain value V1. Next, another function (again) EM(t) is plotted, now from the time T=T2 and beginning at the value V1. Thereto, the function EM(t−T2) has been shifted over a constant C2 to reflect the starting at a non-zero value. This comes down to the constant mentioned in claim 4. This next function is cut off at T3, where the whole procedure is repeated, and so on, until the point in time "Tdesired" has been reached. The resulting function ER(t) can now be integrated over the desired period T0 through Tdesired. Obviously, this will often be a 24 hour period, but it can be any desired period, as long as it is likely that sufficient data points can be gathered in the time in between.

Note that for the construction method for ER(t) it follows that there is always the same maximum value X. This slightly unnatural behavior is not present in adapted construction methods, still according to the invention. For example, it is possible to not cut off the function EM(t−T1) after T2, but let it continue, and simply add another function (EM(t−T2) on top of it from T2, and so on. Then the peaks will be higher, up to a maximum, when the first function EM(t−T1) has fallen to zero sufficiently. Furthermore, the invention also encompasses a dynamic (re)determination of EM(t) when new data are added. This may also ensure that, according to the method described for FIG. 3, the peak height may be adapted to these new data, providing for more accuracy.

Figure 5:
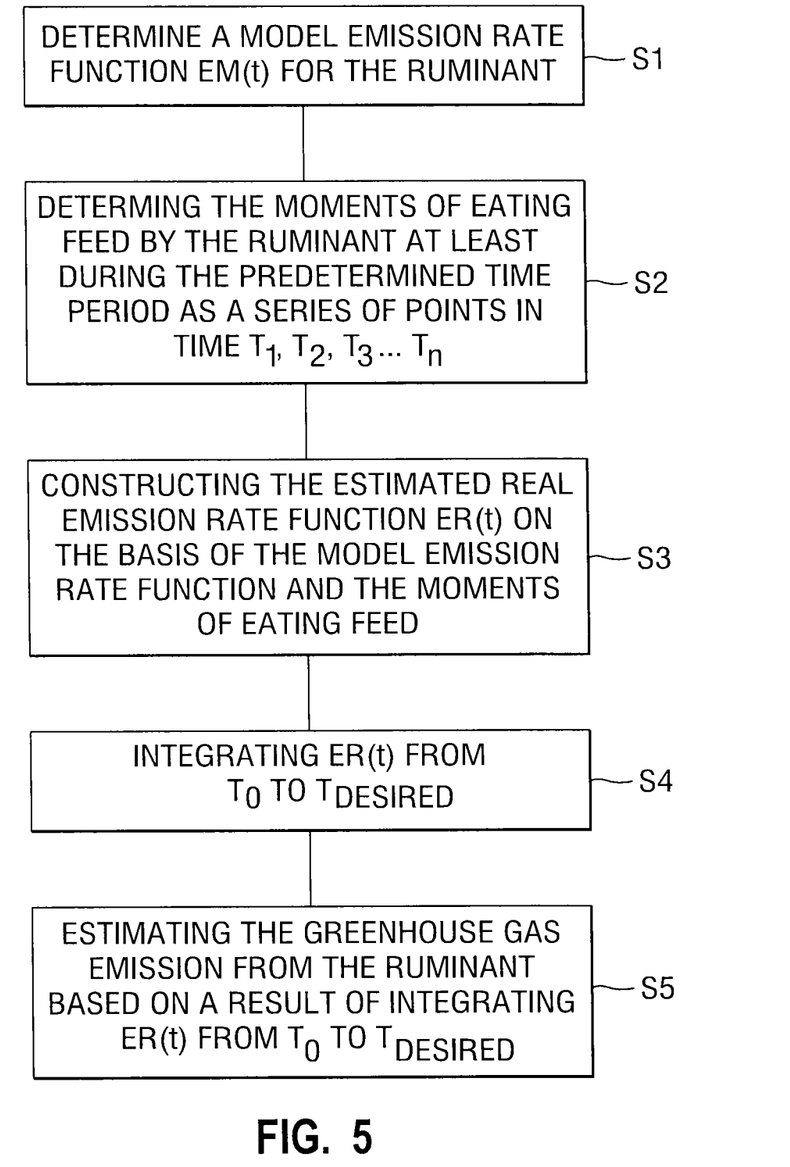
FIG. 5 is a figure illustrating a process flow according to an embodiment.

According to one embodiment illustrated in FIG. 5, there is illustrated an exemplary method for estimating a greenhouse gas emission from a ruminant in a loose housing environment, and in a predetermined time period from T0 to Tdesired. In step S1, a model emission rate function EM(t) for the ruminant is determined. In step S2, the moments of eating feed by the ruminant, at least during the predetermined time period, are determined as a series of points in time $\{T1, T2, T3, \ldots, Tn\}$. In step S3, the estimated real emission rate function ER(t) is constructed on the basis of the model emission rate function and the moments of eating feed. In step S4, ER(t) is integrated from T0 to Tdesired and in step S5 the greenhouse gas emission from the ruminant is estimated based on a result of integrating ER(t) from T0 to Tdesired.

Further modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A method for estimating a greenhouse gas emission from a ruminant in a loose housing environment, and in a predetermined time period from T0 to Tdesired, the method implemented by particularly programmed processing circuitry comprises:
    determining a model emission rate function EM(t) for the ruminant;
    determining the moments of eating feed by the ruminant, at least during the predetermined time period, as a series of points in time $\{T1, T2, T3, \ldots, Tn\}$;
    constructing the estimated real emission rate function ER(t) on the basis of the model emission rate function and the moments of eating feed;
    integrating ER(t) from T0 to Tdesired; and
    estimating the greenhouse gas emission from the ruminant based on a result of integrating ER(t) from T0 to Tdesired.

2. The method of claim 1, wherein the function ER(t) is constructed as ER(t)=EM(t−T1−C1) for T1.ltoreq.t<T2, EM(t−T2−C2) for T2.ltoreq.t<T3, . . . , EM(t−Tn−1−Cn−1) for Tn−1.ltoreq.t<Tn, and EM(t−Tn−Cn) for Tn.ltoreq.t, wherein C1, C2, . . . , Cn are constants.

3. The method of claim 1, wherein the function ER(t) is constructed as $$ER(t) = \sum_{i=1}^{n} EM(t - Ti)$$

for all eating moments T1, . . . , Tn relevant for the desired period of time T0-Tdesired.

4. The method of claim 1, wherein determining the moments of eating feed comprises determining the moments when at least one of the following conditions is met: new ration is provided to the ruminant feed is displaced towards a feed fence at which the ruminant is allowed to feed the ruminant is provided access to a pasture.

5. The method of claim 1, comprising:
    providing a herd having a plurality of ruminants providing one or more ruminant ID devices, at least at one or more positions for feeding the ruminants and at one or more positions for measuring a greenhouse gas emission rate and arranged to identify the ruminant and provide an ID signal performing the method for each of the ruminants in the herd, and
    estimating a total greenhouse gas emission in the predetermined time period as the sum of the greenhouse gas emissions from each of the ruminants.

6. The method of claim 1, further comprising:
controlling the greenhouse gas emission of the ruminant based on the estimated greenhouse gas emission.

7. The method of claim 2, wherein all constants C1 ... Cn are determined such that the function ER(t) is a continuous function.

8. The method of claim 1, wherein all constants are zero.

9. The method of claim 1, wherein determining the moments of eating comprises identifying the ruminant at a feeding place and determining that said ruminant is eating, by way of a eating sensor.

10. The method of claim 9, wherein the eating sensor comprises a camera with image processing software for recognizing eating behaviour, a feed weight sensor arranged to determine a weight change in a feeding device, or a microphone with sound processing software for recognizing eating behaviour.

11. The method of claim 1, wherein the feed is ration containing roughage.

12. The method of claim 11, wherein the feed further contains concentrates.

13. The method according to claim 12, wherein the mathematical curve is selected from a set of standard curves depending on the type or race of animal, and wherein the fitting comprises multiplying the curve by a constant (F).

14. The method of claim 1, wherein determining the model emission rate function comprises: measuring a greenhouse gas emission rate at a plurality of measurement points in time TM0, ..., TMn, providing respective values EM0, ..., EMn establishing for each of said measurement points in time TM0, ..., TMn the most recent feeding moment TF0, ..., TFn before the respective measurement point in time, and determining the function ER(t) by fitting a mathematical curve that fits through the sets of values ((TM0−TF0), EM0), ..., ((TMn−TFn), EMn).

15. The method of claim 14, further comprising repeating the steps of measuring at an additional point in time Tadd said greenhouse gas emission rate EMadd, and redetermine the function by adapting and refitting the mathematical curve through one of the last X sets of values of TM and EM, wherein X is a predetermined number, and all sets of values of TM and EM.

16. The method of claim 15, wherein, in the step of redetermining the function, one or more predetermined constraints are applied, comprising predetermined rules with respect to the relative or absolute change of one or more coefficients used in the function.

17. The method of claim 1, wherein determining the moments of eating comprises determining when the ruminant produces eating sounds by way of a sound sensor, that is designed to detect sounds produced by the ruminant when moving its mouth in particular for chewing.

18. The method of claim 17, wherein, when determining the moments of eating, rumination sounds are excluded.

19. The method of claim 17, wherein, when determining the moments of eating, only rumination sounds are detected, and the moments of eating are determined to be the moments of a local minimum in rumination sounds.

20. A greenhouse gas emission estimation device for estimating a greenhouse gas emission from a ruminant, the device comprising:
at least one greenhouse gas emission rate sensor, arranged to provide a greenhouse gas emission rate signal;
a clock device arranged to provide a time signal each time when said ruminant eats and each time when the at least one greenhouse gas emission rate sensor measures a greenhouse gas emission rate signal; and
particularly programmed processing circuitry configured to
determine a model emission rate function EM(t) for the ruminant,
determine the moments of eating feed by the ruminant, at least during a predetermined time period, as a series of points in time {T1, T2, T3, ..., Tn},
construct an estimated real emission rate function ER(t) on the basis of the model emission rate function for the ruminant and the moments of eating feed by the ruminant,
integrate ER(t) from T0 to Tdesired, and
estimate the greenhouse gas emission from the ruminant based on a result of integrating ER(t) from T0 to Tdesired.

21. The device of claim 20, wherein each greenhouse gas emission rate sensor comprises or is provided together with a ruminant ID device arranged to establish the ID of a ruminant upon visiting the sensor.

22. The device of claim 20, comprising a feeding unit with an animal ID station arranged to identify the ruminant upon feeding, the control unit arranged to process the corresponding time signal together with the animal ID.

23. The device of claim 22, wherein there is provided a greenhouse gas emission sensor with an animal ID station at one or more of a milking place, at a feeding place or at a resting place.

* * * * *